United States Patent [19]

Urban

[11] Patent Number: 5,206,367

[45] Date of Patent: Apr. 27, 1993

[54] PREPARATION OF OPTICALLY ACTIVE SPIRO-HYDANTOINS

[75] Inventor: Frank J. Urban, Waterford, Conn.

[73] Assignee: Pfizer Inc., New York, N.Y.

[21] Appl. No.: 837,794

[22] Filed: Feb. 18, 1992

[51] Int. Cl.$^5$ ............... C07D 215/48; C07D 471/10
[52] U.S. Cl. ....................................... 546/15; 546/170
[58] Field of Search ................. 546/15, 163, 159, 135, 546/170

[56] References Cited

U.S. PATENT DOCUMENTS

| 4,130,714 | 12/1978 | Sarges | 548/309 |
| 4,345,083 | 8/1982 | Rasmussen | 546/163 |
| 4,435,578 | 3/1984 | Cue, Jr. et al. | 548/309 |
| 4,716,113 | 12/1987 | Urban | 435/125 |
| 4,952,694 | 8/1990 | Brackeen et al. | 546/15 |

FOREIGN PATENT DOCUMENTS

84/01767 10/1984 PCT Int'l Appl. ................. 548/309

OTHER PUBLICATIONS

Journal of Organic Chemistry, vol. 47, p. 4081 (1982), Sarges et al.

Primary Examiner—Robert W. Ramsuer
Assistant Examiner—Joseph K. McKane
Attorney, Agent, or Firm—Peter C. Richardson; Paul H. Ginsburg; Valerie Fedowich

[57] ABSTRACT

This invention relates to the preparation of preparing optically-active asymmetric spiro-hydantoin compounds, which are known to be of value in the medical control of certain chronic diabetic complications arising from diabetes mellitus. This invention also includes within its scope certain corresponding novel amino and hydantoic acid compounds and the cinchonine salt of optically active hydantoic acid, which are used as intermediates in the aforesaid process.

14 Claims, No Drawings

PREPARATION OF OPTICALLY ACTIVE SPIRO-HYDANTOINS

BACKGROUND OF THE INVENTION

This invention relates to the synthesis and resolution of a racemic spiro-hydantoin compound into its optical antipodes. More particularly, it is concerned with the preparation of various optically-active asymmetric sprio-hydantoin compounds, which are known to be of value in the medical control of certain chronic diabetic complications arising from diabetes mellitus. The invention also includes within its scope certain corresponding novel amino and hydantoic acid compounds and the cinchonine salt of optically active hydantoic acid, which are used as intermediates in the aforesaid process.

It is now known that certain optical isomers of various asymmetric spiro-hydantoin compounds are useful as aldose reductase inhibitors and, hence, of value in the treatment of certain chronic diabetic complications such as diabetic cataracts, neuropathy and retinopathy. Included among these agents are such optically-active compounds as (4S)-(+)-6-fluoro-2,3-dihydro-spiro[4H-benzopyran-4,4'-imidazolidine]-2',-5'-dione (sorbinil), which is described in U.S. Pat. No. 4,130,714 and (5'S)-3'-chloro-5',6',7',8'-tetrahydro-spiro-[imidazolidine-4,5'-quinoline]-2,5-dione which is disclosed in European Patent Application No. 180,421.

In the past, these optically active compounds have been obtained by various means. For instance, sorbinil was first obtained after resolution of the corresponding dl-compound with l-brucine and reported as d-6-fluoro-spiro-[chroman-4,4'-imidazolidine]-2",5'-dione in U.S. Pat. No. 4,130,714. Later synthetic developments involved the use of asymmetric induction starting with a ketone precursor (viz., 6-fluoro-2,3-dihydro-4H-1-benzopyran-4-one) and optically-active (S)-α-methylbenzylamine in the presence of titanium tetrachloride, as reported in the *Journal of Organic Chemistry*, Vol. 47, p. 4081 (1982) and thereafter obtained by cyclization of S-6-fluoro-4-ureidochromane-4-carboxylic acid, which is in turn obtained by resolution of racemic 6-fluoro-4-ureido-chroman-4-carboxylic acid via diasterometic salts with either D-(+)-(1-phenethyl)amine or L-(−)ephedrine in U.S. Pat. No. 4,435,578; while in U.S. Pat. No. 4,716,113 there is described a multi-step process for preparing sorbinil, starting from 2-(4'-fluorophenoxy)ethyl bromide, wherein the enzyme α-chymotrypsin is employed to resolve the intermediate known as methyl 4-amino-6-fluorochroman-4-carboxylate into its respective optical antipodes prior to conversion to the desired spiro-hydantoin ring compound via treatment with an alkali metal cyanate in an acid medium.

More recently, a three step process for resolving a racemic sprio-hydantoin compound was reported in U.S. Pat. No. 4,952,694. This process involves reacting said racemic compound with an optically-active asymmetric isocyanate to form the corresponding diastereomeric uredio compound. Separated ureido diastereomers are converted to the corresponding asymmetric hydantoin compounds by treatment with an alkali metal lower alkoxide followed by acidification, whereupon the desired optical isomer is obtained.

SUMMARY OF THE INVENTION

The present invention relates to the process for the synthesis and resolution of racemic compounds into optically active spiro-hydantoins of the formula

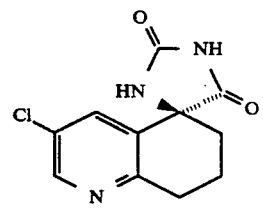

comprising (a) reacting a compound of the formula

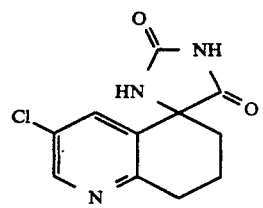

with a base to form the compound of the formula

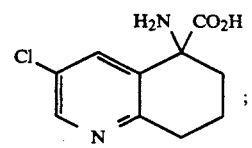

(b) reacting said compound of the formula IX with an alkali metal cyanate to form a compound of the formula

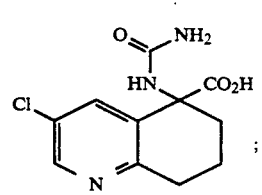

(c) resolving said compound of the formula X with optically active cinchonine to form a compound of the formula

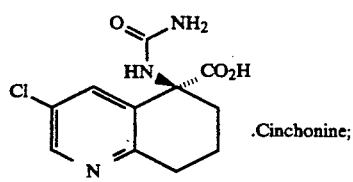

and (d) reacting said compound of the formula XI with acid to form said compound of the formula I.

The present invention also relates to novel intermediates used in the foregoing process. The present invention therefore relates to a compound of the formula

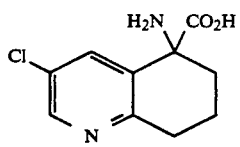
The present invention also relates to a compound of the formula
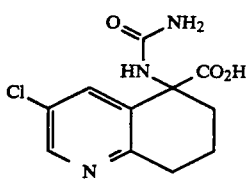
The present invention also relates to a compound of the formula
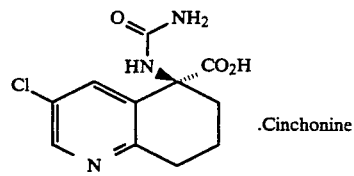
The present invention also relates to a compound of the formula
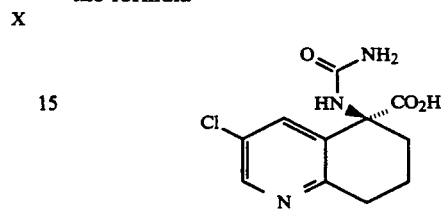
DETAILED DESCRIPTION
The following reaction scheme illustrates the processes of the present invention.
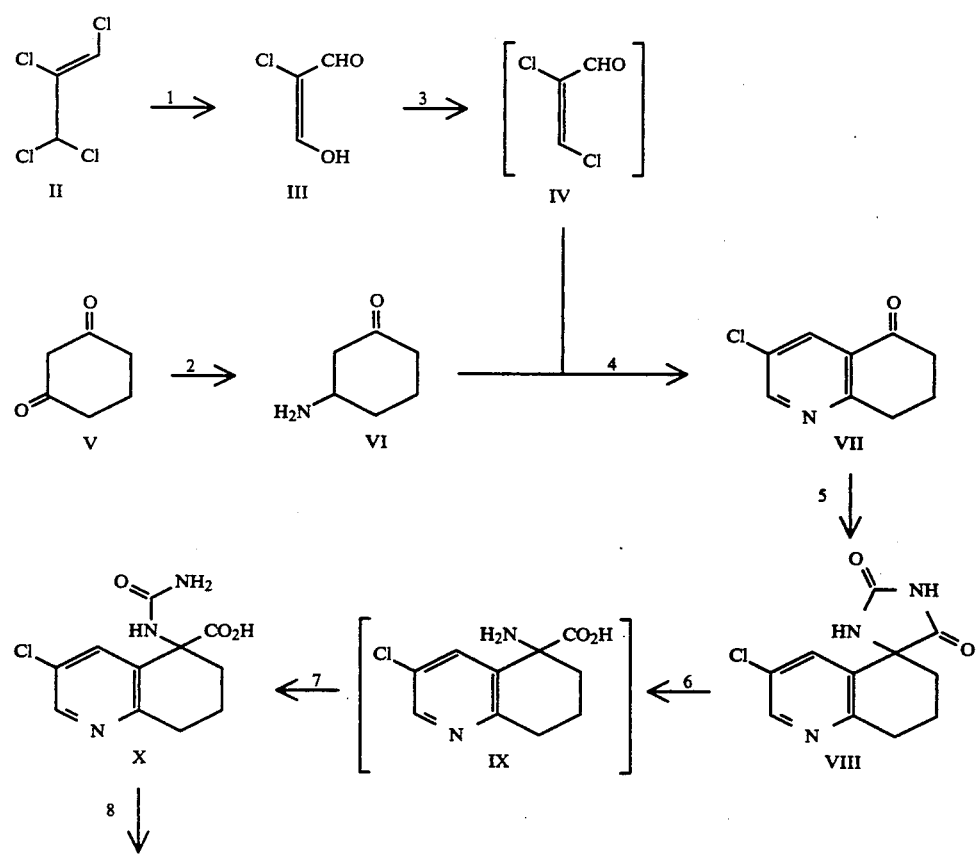

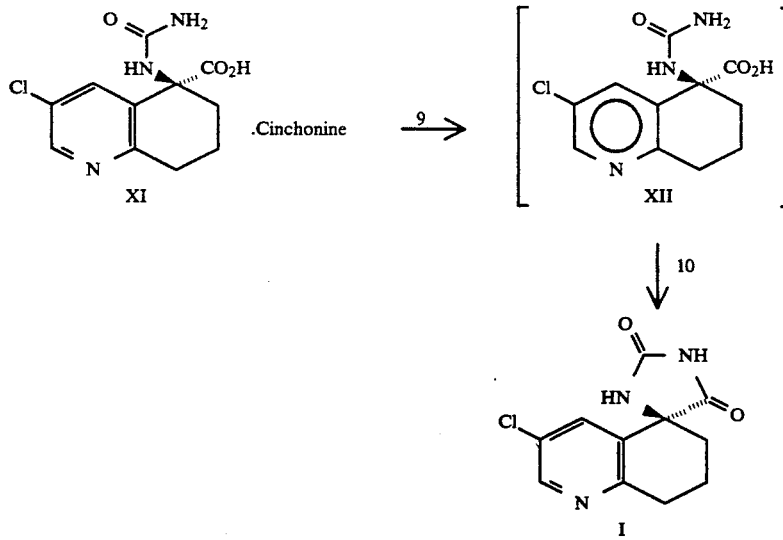

-continued

In reaction 1 of Scheme 1, 1,2,3,3-tetrachloropropene of formula II is converted to the corresponding chloromalondialdehyde III by adding the compound of formula II to concentrated sulfuric acid. The reaction mixture is heated slowly to between about 40° C. to about 50° C., preferably about 45° C., and the temperature is maintained for a time period between about 12 hours to about 16 hours.

In reaction 2 of Scheme 1, the 1,3-cyclohexane dione of formula V is heated to reflux and reacted with ammonia gas in a refluxing solvent, (e.g., benzene or toluene), to remove water in the reaction mixture as an azeotrope to obtain the corresponding 1-amino-cyclohexan-3-one of formula VI.

In reaction 3 of Scheme 1, a solution of oxalyl chloride in methylene chloride is added dropwise to a solution of chloromalondialdehyde III in methyene chloride and a phase transfer catalyst, such as dimethylformamide, under inert reaction conditions. The reaction mixture is stirred at room temperature until conversion to the corresponding 2,3-dichloroacrolein is complete. In reaction 4 of Scheme 1, a solution of 1-amino-cyclohexan-3-one VI in dimethylformamide is added dropwise to the above acrolein to form the corresponding 3-chloro-5,6,7,8-tetrahydroquinolin-5-one VII. The reaction, generally carried out overnight, will be in the temperature range between about 60° C. to about 80° C., preferably about 70° C.

In reaction 5 of Scheme 1, the compound of formula VII is condensed with an alkali metal cyanide (e.g., sodium cyanide or potassium cyanide) and ammonium carbonate to form a racemic spirohydantoin of formula VIII. This reaction is normally carried out in the presence of an inert polar organic solvent medium in which both the reactant and reagents are mutually miscible. Preferred organic solvents include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylformamide, N,N-diethylformamide and N,N-dimethylacetamide. In general, the reaction is conducted at a temperature that is in the range of from about 20° C. up to about 120° C. for a period of about two hours to about four days. Although the amount of reactant and reagents employed in the reaction can vary to some extent, it is preferable to employ at least a slight molar excess of the alkali metal cyanide reagent with respect to the carbonyl ring compound starting material in order to effect maximum yield. Upon completion of the reaction, the product is easily isolated in a conventional manner, e.g., by first diluting the reaction mixture with water and then cooling the resultant aqueous solutions to room temperature, followed by acidification to afford the racemic 3-chlorospiro-[5,6,78-tetrahydroquinolin-5,4'-imidazolidine]-2',5'-dione compound VIII in the form of a readily-recoverable precipitate.

In reaction 6 of Scheme 1, the compound of formula VIII is converted to the corresponding 5-amino-3-chloro-5,6,7,8-tetrahydroquinoline-5-carboxylic acid IX. This is accomplished by heating VIII with base (e.g., barium hydroxide, potassium hydroxide, sodium hydroxide) in an aqueous medium at reflux, the heating is preferably conducted for a time period between about 36 hours to about 60 hours, more preferably 48 hours. The product is preferably isolated by reacting the solution with ammonium carbonate at a temperature between about 40° C. to about 60° C., more preferably at 50° C. Preferably, the filtrate of the aqueous suspension is evaporated and recrystallized in an isopropanol/ether solution to afford the corresponding 5-amino-3-chloro-5,6,7,8-tetrahydroquinoline-5-carboxylic acid IX. Where the process for the preparation of 3-chloro-5-ureido-5,6,7,8-tetrahydroquinoline-5-carboxylic acid X is performed in one reaction vessel, this isolation step is not performed.

In reaction 7 of Scheme 1, the compound of formula IX is converted to the corresponding compound of formula X by adding an alkali metal, (e.g., sodium cyanate or potassium cyanate), to the 5-amino-3-chloro-5,6,7,8-tetrahydroquinoline-5-carboxylic acid aqueous reaction solution. Preferably, the reaction mixture is stirred at room temperature for approximately four hours and at a temperature between about 40° C. to about 80° C., more preferably 60° C., for a time period between about 10 hours to about 14 hours, more preferably 12 hours. An alkali metal is again added and the reaction mixture at a temperature between about 40° C.

to about 80° C., more preferably 60° C., is stirred for an additional time period between about 36 hours to about 60 hours, more preferably 48 hours. Upon completion of this reaction step, the desired 3-chloro-5-ureido-5,6,7,8-tetrahydroquinoline-5-carboxylic acid X is easily recovered from the reaction mixture by any number of conventional techniques and most preferably by first filtering same and then extracting by acidifying the chilled aqueous mixture so as to precipitate the desired product therefrom.

In reaction 8 of Scheme 1, the racemic modification of formula X is converted by an optically active alkaloid, (+)-cinchonine, into a mixture of diastereomers which can then be separated into its component parts. This is preferably accomplished by heating to reflux a methanol slurry of the racemic 3-chloro-5-ureido-5,6,7,8-tetrahydroquinoline-5-carboxylic acid X and (+)-cinchonine to form a thick white solid precipitate. At this point, acetonitrile in added and the mixture refluxed overnight. The filtrate is collected at a temperature between about 45° C. to about 65° C., more preferably about 55° C. The solids taken up in a methanol slurry are refluxed for approximately one half hour, acetonitrile added and the solution, in turn, is refluxed overnight. Upon completion of this reaction step, the desired optically pure cinchonine salt is easily recovered from the reaction mixture by filtering the solution at a temperature between about 45° C. to about 75° C., more preferably about 60° C.

In reaction 9 of Scheme 1, the compound of formula XI is suspended in an aqueous medium and treated with acid to obtain the corresponding optically active hydantoic acid of formula XII. The product is easily isolated in the form of a readily recoverable solid, however, where the process for the preparation of 5S-3-chlorospiro-[5,6,7,8-tetrahydroquinolin-5,4'-imidazolidine]-2',5'-dione of formula I is performed in one reaction vessel, this isolation step is not performed.

Reaction 10 of Scheme 1 involves converting the separated ureido diastereomers obtained in reaction 8 to the corresponding optically-active hydantoin compound by treatment with an acid, (e.g., glacial acetic acid, aqueous phosphoric acid or aqueous sulfuric acid). Preferably, a solution of a diastereomer is heated to a temperature between about 80° C. to about 120° C., preferably 100° C.

Hence, the novel process of the present invention now provides the required optically-active spiro-hydantoin compound discussed above in pure form and in high yield by a unique method, which represents a major improvement over prior art methods in view of the ease of synthesis and the greatly reduced costs involved.

The optically active spiro-hydantoin final product of this invention, 5S-3-chlorospiro-[5,6,7,8-tetrahydroquinolin-5,4'-imidazolidine]-2',5'-dione, is useful as an aldose reductase inhibitor for the control of chronic diabetic complications, in view of its ability to reduce lens sorbitol levels in diabetic subjects. The spiro-hydantoin can be administered by either the oral or parenteral route of administration. The compound is generally administered in dosages ranging from about 0.1 mg to about 10 mg per kg of body weight per day, although variations will necessarily occur depending upon the weight and condition of the subject being treated and the particular route of administration chosen.

The compound may be administered either alone or in combination with pharmaceutically acceptable carriers by either of the routes previously indicated, and such administration can be carried out in both single and multiple dosages. More particularly, the compound can be administered in a wide variety of different dosage forms, i.e., it may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for just such purposes. In general, the compound is present in such dosage forms at concentration levels ranging from about 0.5% to about 90% by weight of the total composition, i.e., in amounts which are sufficient to provide the desired unit dosage.

EXAMPLE 1

1-Amino cyclohexene-3-one 1,3-Cyclohexane dione (44.5 grams, 0.4 mol) was suspended in benzene (500 ml) in a 1 L flask equipped with mechanical stirrer, gas inlet tube, and Dean-Stark trap with reflux condenser. The mixture was heated to reflux to give a solution and ammonia gas was bubbled through the reaction until the theoretical amount of water had collected in the Dean Stark trap. The reaction mixture was cooled to room temperature and the solid was filtered. The yield was 44 g (99%) of a tan solid; mp 120°-125° C. The reaction can be monitored by thin layer chromatography on silica gel plates with $CHCl_3$: methanol: acetic acid 90:5:5. If the initial product is not a uniform solid, it can be slurried in hot ethyl acetate, cooled and collected.

EXAMPLE 2

Chloromalondiaudehyde 1,1,2,3-Tetrachloropropene (206 grams, 1.14 mol) was added to concentrated sulfuric acid (210 ml) to give a two phase mixture. This was heated slowly to 40°-50° C. while the reaction mixture became homogeneous and darkened to a brown solution. The temperature was maintained for 12 hours or overnight for convenience. The reaction was cooled with a dry ice/acetone bath to −10° C. and stirred while ice chips were added, very slowly initially, then at a faster rate after ¼ of a total of 450 grams of ice was added. The rate of ice addition was such that the internal temperature was less than −5° C. The reaction was granulated at −20° C. for ½ hour before the dark solid was filtered and sucked dry on the filter without washing. The solid was dissolved in ethyl acetate (600 ml) and washed 2 times with ½ saturated sodium chloride solution. (If saturated NaCl was used to wash out the sulfuric acid residues, some solid NaCl precipitated in the separatory funnel). The organic solution was dried over magnesium sulfate and decoloizing carbon (Darco (Trademark)). The solution was filtered and evaporated to a wet solid in vacuo. Methylene chloride was added to the solid and vacuum stripping was continued. The methylene chloride slurry was diluted with hexanes and the solid product was collected, 46.14 grams 38% yield mp 152°-50° C. (dec). The lower result may have been due to incomplete hydrolysis since

EXAMPLE 3

3-Chloro-5,6,7,8-tetrahydroquinolin-5-one

Chloromalondialdehyde (19 grams, 0.178 mol) was suspended in methylene chloride (100 ml) with dry dimethylformamide (DMF) (2.5 ml). This was mechanically stirred under a nitrogen atmosphere while a solution of oxalyl chloride (23.7 grams/16.3 ml, 0.185 mol) in methylene chloride (50 ml) was added dropwise over 20 minutes. The reaction mixture at first started to warm from 22° to 28°, but as the evolution of gases increased the temperature fell to 18°. The reaction was stirred at room temperature and was followed by thin layer chromatography (ethyl acetate/hexanes, 1:1) until conversion to 2,3-dichloroacrolein was complete. A solution of 1-amino-cyclohexen-3-one (19.85 grams, 0.18 mol) in DMF (125 ml) was added dropwise and the reaction was heated to 70° C. overnight. The reaction mixture was cooled to room temperature, diluted with saturated NaHCO$_3$, and twice extracted with ethyl acetate (400 ml and 200 ml). The combined organic layers were washed with water (3×) and brine (1×). The organic solution was stirred with MgSO$_4$ and decolorizing carbon (Darco (trademark)); then filtered through Super Cel (trademark)) and concentrated to a brown solid. Yield 21 grams (65%); mp 90°–91° C. NMR (CDCl$_3$, 300 MHz) δ8.6 (d, 1), 8.24 (d, 1), 3.1 (t, 2), 2.7 (m, 2), 2.15 (m, 2).

EXAMPLE 4

3-Chlorospiro-[5,6,7,8-tetrahydroquinolin-5,4'-imidazolidine]-2',5'-dione

3-Chloro-5,6,7,8-tetrahydroquinolin-5-one (125 grams, 0.689 mol) was suspended in formamide (98%, 1 L) with sodium bisulfite (73 grams, 0.7 mol). The mixture was mechanically stirred while ammonium carbonate (285 grams, 2.97 mol) was added in portions. This caused some foaming which limited the rate of addition. After the initial foaming subsided, potassium cyanide (90 grams, 1.38 mol) was added in one portion as a solid. The reaction mixture was stirred at room temperature for 3 days. The reaction was diluted with water (500 ml) and cooled in an ice water bath. The reaction pH was 9.91. 6N HCl (about 550 ml) was added dropwise to give a stable pH of 7.2. Again there was some foaming toward the end of the pH adjustment and the gases were scrubbed with a caustic trap. Water (500 ml) was added to further dilute the reaction and the mixture was granulated for ½ hour. The product was filtered and air dried overnight. The crude solid was broken up and slurried in acetonitrile (600 ml) for 45 minutes. The solid product was filtered, washed with acetonitrile and dried in vacuo at 40° C. Yield 134 grams (77.5%); mp 230°–3° C. NMR (DMSO, d$_6$, 300 MHz) δ10.7 (bs, 1), 8.6 (s, 1), 8.5 (d, 1), 7.65 (d, 1), 2.9 (t, 2), 2.15 (m, 2), 1.9 (m, 2).

EXAMPLE 5

5-amino-3-chloro-5,6,7,8-tetrahydroquinoline-5-carboxylic acid

3-Chlorospiro-[5,6,7,8-tetrahydroquinolin-5,4'-imidazolidine]-2',5'-dione, (20 grams, 0.0795 mol) and barium hydroxide (50 grams, 0.159 mol) in water (300 ml) were heated at reflux for 48 hours. The solution was cooled to 50° C. and ammonium carbonate (16 grams, 0.167 mol) was added in portions. After 0.5 hours, the aqueous suspension was filtered and the solids washed with warm water. The filtrate was evaporated in vacuo to a solid. This was slurried in isopropanol (200 ml) was the solvent was again evaporated. The residual solid was suspended in isopropanol (125 ml) and ether (125 ml), granulated for 1 hour, and collected by filtration. The amino acid was dried in vacuo; 13.68 grams, 75% yield. mp 213°–14.5° C. (dec.) NMR (DMSO-d$_6$, 300 MHz) δ8.46 (d, 1), 7.88 (d, 1), 3.5 (br s, NH$_3$), 2.80 (t, 2), 2.27 (m, 1), 2.10 (m, 1), 1.88 (m, 2).

EXAMPLE 6

3-chloro-5-ureido-5,6,7,8-tetrahydroquinoline-5-carboxylic acid

3-Chlorospiro-[5,6,7,8-tetrahydroquinolin-5,4'-imidazolidine]-2',5'-dione (133.2 grams, 0.53 mol) and sodium hydroxide (70 grams, 1.75 mol) in water (500 ml) was refluxed for 48 hours. The reaction was cooled to 20° C. and the pH adjusted to about 7 by the addition of HCl (first conc. HCl, then 3N as neutrality is reached). Potassium cyanate (8.59 grams, 1.06 mol) was added carefully in portions over 30 minutes and the reaction stirred at room temperature for 4 hours, then at 60° C. overnight. Additional potassium cyanate (40 grams, 0.53 mol) was added in the morning and the reaction stirred for 48 hour at 60° C. During the reaction with cyanate, the pH of the reaction became basic and was periodically adjusted to ca. pH 7.5. The reaction mixture was stirred with a small amount of activated carbon and filtered. The filtrate was cooled to 5° to 10° C. and acidified to pH 3.5 with 6N HCl. The precipitate was collected, washed with water and slurried in acetone (500 ml). The product was filtered and dried in vacuo. 96 grams; 67.3% yield. mp 188°–89.5° C. NMR (DMSO-d$_6$, 300 MHz) δ8.43 (d, 1), 7.94 (d, 1), 6.92 (s, 1), 5.72 (s, 1), 2.83 (t, 2), 2.26 (m, 1), 2.12 (m, 1), 1.90 (m, 2).

EXAMPLE 7

Resolution of 3-chloro-5-ureido-5,6,7,8-tetrahydroquinoline-5-carboxylic acid The racemic ureido acid (95 g, 0.353 mol) and cinchonine (103.85 g, 0.353 mol) were suspended in methanol (600 ml) and the mixture heated to reflux. As the slurry was being heated, it became more fluid at first and then a thick white solid precipitated. At this point, acetonitrile (2 L) was added in a slow stream and the mixture was refluxed overnight. The heat was removed and the solids were collected at about 55° C. This precipitate (90.5 grams, 45.5% yield) was suspended in refluxing methanol (500 ml) for 0.5 hours, then acetonitrile (2 L) was added and the slurry was refluxed overnight. Filtration of the solid at 60° C. afforded the optically pure cinchonine salt; 72.12 grams, 36% yield. mp 221°–3° C. [α]$_D$+144.09° (c 0.499, MeOH).

EXAMPLE 8

5S-3-chloro-5-ureido-5,6,7,8-tetrahydroquinoline-5-carboxylic acid

The resolved cinchonine salt (0.72 grams, 1.28 mmol) was suspended in water (10 ml) and stirred for approximately 10 minutes with ice bath cooling while in HCl was added dropwise to lower the pH of the solution to 3.5. The product was collected as a white solid and dried overnight in vacuo; 0.34 grams, 99% yield. m.p.

204°–5° C. (dec.). NMR (DMSO-d$_6$, 300 MHz) δ8.43 (d, 1), 7.94 (d, 1), 6.92 (s, 1), 5.72 (s, 1), 2.83 (t, 2), 2.26 (m, 1), 2.12 (m, 1), 1.90 (m, 2).

EXAMPLE 9

5S-3-Chlorospiro-[5,6,7,8-tetrahydroquinolin-5,4'-imidazolidine]-2',5'-dione

The resolved cinchonine salt (75 grams, 0.133 mol) was suspended in glacial acetic acid (1 L) and the solution was heated to about 100° C. After 2 hours, solution was achieved and thin layer chromatography showed complete conversion to the hydantoin. The reaction was concentrated in vacuo to a low volume and resulting oil stirred while water (400 ml) was added to precipitate the hydantoin. The crude hydantoin was purified by dissolving in hot 95% ethanol (225 ml) with activated carbon, filtering the solution and adding water (500 ml). The crystalline product was collected, washed with water, and dried under vacuum at 40° C.; 30.2 grams, 90% yield. mp 262°–67° C. [α]$_D$+41.8° (c 0.517, methanol). NMR (DMSO-d$_6$, 300 MHz) δ11.0 (br s, 1), 8.6 (s, 1), 8.52 (d, 1), 7.65 (d, 1), 2.85 (t, 2), 2.13 (m, 2), 1.95 (m, 2).

I claim:

1. The method of preparing a compound of the formula

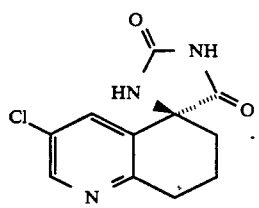

I comprising reacting a compound of the formula

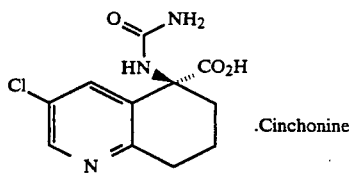

XI with acid at an elevated temperature.

2. The method of claim 1, wherein said acid is glacial acetic acid, aqueous phosphoric acid or aqueous sulfuric acid.

3. The method of claim 1, wherein said temperature is between about 80° C. and about 120° C.

4. The method of claim 1 wherein said compound of the formula

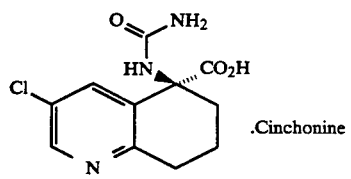

XI is prepared by reacting a compound of the formula

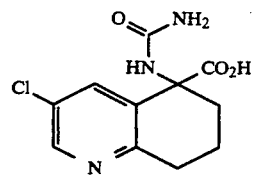

X with an (+)-cinchonine.

5. The method of claim 4 wherein said compound of the formula

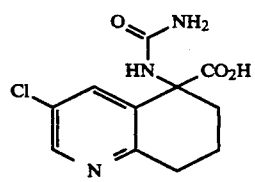

X is prepared by reacting a compound of the formula

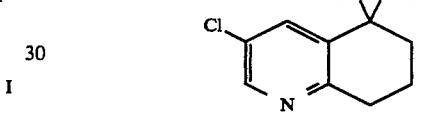

IX with an alkali metal cyanate.

6. The method of claim 5, wherein said alkali metal cyanate is sodium cyanate or potassium cyanate.

7. The method of claim 5 wherein said compound of the formula

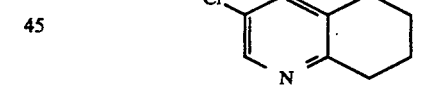

IX is prepared by reacting the racemic compound of the formula

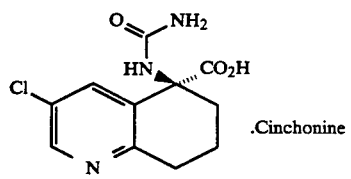

VIII with base.

8. The method of claim 7, wherein said base is barium hydroxide, potassium hydroxide or sodium hydroxide.

9. The method of preparing a compound of the formula comprising reacting a compound of the formula
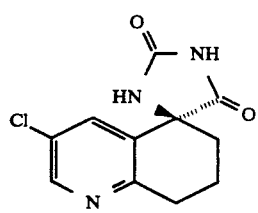
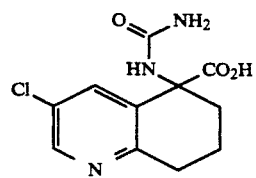
with an (+)-cinchonine followed by treatment with an acid.
10. The method of claim 9, wherein the acid is glacial acetic acid, aqueous phosphoric acid or aqueous sulfuric acid.
11. A compound of the formula
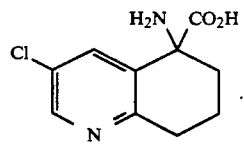
12. A compound of the formula
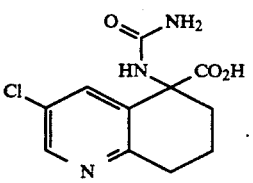
13. A compound of the formula
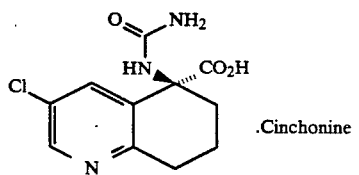
14. A compound of the formula
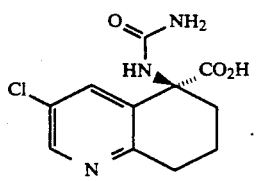
* * * * *